(12) United States Patent
Suzuki

(10) Patent No.: US 7,166,115 B2
(45) Date of Patent: Jan. 23, 2007

(54) LIGATION TREATING APPARATUS

(75) Inventor: Hirohito Suzuki, Ibaraki (JP)

(73) Assignee: Kabushiki Kaisha Top, Tokyo (JP)

( * ) Notice: Subject to any disclaimer, the term of this patent is extended or adjusted under 35 U.S.C. 154(b) by 57 days.

(21) Appl. No.: 10/513,687

(22) PCT Filed: Aug. 5, 2003

(86) PCT No.: PCT/JP03/09919

§ 371 (c)(1),
(2), (4) Date: Nov. 8, 2004

(87) PCT Pub. No.: WO2004/017840

PCT Pub. Date: Mar. 4, 2004

(65) Prior Publication Data

US 2005/0177178 A1    Aug. 11, 2005

(30) Foreign Application Priority Data

Aug. 26, 2002 (JP) .............................. 2002-244577

(51) Int. Cl.
*A61B 17/10* (2006.01)

(52) U.S. Cl. ........................ 606/140; 606/139; 606/144

(58) Field of Classification Search ................ 606/144, 606/140, 139
See application file for complete search history.

(56) References Cited

U.S. PATENT DOCUMENTS 5,980,537 A * 11/1999 Ouchi .......................... 606/140
6,464,708 B1 * 10/2002 Higuma et al. ............. 606/140

FOREIGN PATENT DOCUMENTS

| EP | 1 147 744 A2 | 10/2001 |
| JP | 10-272091 A | 10/1998 |
| WO | WO-94/08517 A | 4/1994 |
| WO | WO-00/10468 A1 | 3/2000 |

* cited by examiner

*Primary Examiner*—(Jackie) Tan-Uyen Ho
*Assistant Examiner*—Natalie Pous
(74) *Attorney, Agent, or Firm*—Birch, Stewart, Kolasch and Birch, LLP

(57) ABSTRACT

A ligation treating apparatus including plurality of ligation rings aligned and held in a cylinder portion which is formed by an inner cylindrical portion and an outer cylindrical portion. A piston member for pushing out the ligation rings is provided in the cylindrical portion. Air introduction means for forcing air into the cylinder portion is also provided. An annular groove for holding the foremost ligation ring is formed at the front end of the inner cylindrical portion. An air discharge port is formed at the bottom of the annular groove. The air discharge port discharges air from the cylinder portion so as to stop the piston member when the ligation ring is moved out of the annular groove.

9 Claims, 4 Drawing Sheets

US 7,166,115 B2

LIGATION TREATING APPARATUS

FIELD OF THE INVENTION

The present invention relates to a ligation treating apparatus which is connected to the tip of an endoscope so as to carry out ligation of varicose vein.

BACKGROUND OF THE INVENTION

Heretofore, a ligation treating apparatus as shown in FIG. 4 is known. This ligation treating apparatus is provided to the tip of an endoscope A and used when ligation of varicose vein in the esophagus or other organs is performed. In a case where multiple varicose veins exist, this ligation treating apparatus is capable of conducting ligation of the multiple varicose veins without the need to take the endoscope in and out of the body cavity of patient.

Hereinafter, the conventional ligation treating apparatus will be described more specifically. This ligation treating apparatus, as shown in FIG. 4, has a plurality of elastically diameter-expanded ligation rings B on an inner cylindrical portion 30 which is connected to the endoscope A. An outer cylindrical portion 31 is provided to the outer side of the inner cylindrical portion 30, and a cylinder portion 32 is formed in space between the inner cylindrical portion 30 and the outer cylindrical portion 31. In the cylinder portion 32, an annular piston member 33 which can move back and forth freely along the external wall of the inner cylindrical portion 30 is provided. Further, a tube 34 is connected to the cylinder portion 32, and fluid is introduced into the cylinder portion 33 via the tube 34. At the base end of the tube 34, a syringe is connected as means for sending fluid forcibly, for example. The tip of the piston member 33 is in direct contact with the rearmost ligation ring B.

To perform ligation, firstly, a varicose vein is sucked into the inner cylindrical portion 30. Then, fluid is introduced into the cylinder portion 32 so as to move the piston member 33 forward. This action causes the piston member 33 to push the ligation rings B forward, and the foremost ligation ring B is released from the front end of the inner cylindrical portion 30 so as to ligate the varicose vein. When other varicose veins are to be ligated without taking the endoscope A out of the body cavity of patient, each of the varicose veins is sucked into the inner cylindrical portion 30 and the above procedure is repeated.

Thereby, a plurality of varicose veins can be ligated in a short time without the need to take the endoscope A in and out of the body cavity of patient. As a result, the pain of the patient can be alleviated.

However, according to the above conventional ligation treating apparatus, there is a possibility that a plurality of ligation rings B may be released from the front end of the inner cylindrical portion 30 simultaneously for a single varicose vein if fluid is introduced abruptly upon operation of the syringe. Accordingly, the syringe must be operated carefully so as to release the ligation rings B from the front end of the inner cylindrical portion 30 one at a time, and such a careful operation of the syringe requires a skilled operator. This is a disadvantage of the conventional ligation treating apparatus.

Thus, an object of the present invention is to eliminate the disadvantage and provide a ligation treating apparatus which has a plurality of ligation rings and is capable of performing ligation on varicose veins on multiple sites quickly and releasing the ligation rings from the front end of an inner cylindrical portion one at a time with certainty.

SUMMARY OF THE INVENTION

To achieve the above object, a ligation treating apparatus of the present invention is provided to the tip of an endoscope so as to carry out ligation of varicose vein and comprises an inner cylindrical portion which is connected to the tip of the endoscope, a plurality of ligation rings which are aligned and held on the circumference of the inner cylindrical portion, and an outer cylindrical portion which surrounds the inner cylindrical portion via the ligation rings and forms a cylinder portion by use of space between the inner cylindrical portion and the outer cylindrical portion. The ligation rings are held on the inner cylindrical portion with diameters thereof elastically expanded and are guided by the inner cylindrical portion and movable toward the front end of the inner cylindrical portion. In the cylinder portion, an annular piston member is provided in direct contact with the rearmost ligation ring and can push the ligation rings toward the front end of the inner cylindrical portion. Further, a first air passage for introducing air into the cylinder portion on the rear side of the piston member is also provided. To the first air passage, air introduction means for forcing air into the cylinder portion is connected. Air introduced into the cylinder portion by the air introduction means via the first air passage drives the piston member forward, thereby pushing the ligation rings toward the front end of the inner cylindrical portion.

Further, an annular groove in which the foremost ligation ring is fitted and held releasably is formed along the circumference of the front end of the inner cylindrical portion. At the bottom of the annular groove, an air discharge port is opened. The air discharge port is communicated with a second air passage which branches off from the first air passage and extends along the inner cylindrical portion.

To carry out ligation of varicose vein or the like by the present invention, firstly, a varicose vein is sucked into the front end of the inner cylindrical portion. Then, with the air discharge port blocked by the foremost ligation ring fitted in the annular groove, a given amount of air is forced into the cylinder portion by the air introduction means via the first air passage. The pressure of the air moves the piston member forward. As the piston member moves forward, it pushes the rearmost ligation ring as well as the rest of the rings forward. Thereby, a ligation ring which is subsequent to the foremost ligation ring pushes the foremost ligation ring out of the annular groove as it moves in a direction to fit in the annular groove. Then, as the foremost ligation ring moves out of the annular groove, it is released from the front end of the inner cylindrical portion and elastically contracts. Thereby, the base of the varicose vein sucked into the front end of the inner cylindrical portion is ligated. Then, the ligation ring subsequent to the ligation ring which has been moved out of the annular groove and released from the front end of the inner cylindrical portion elastically contracts and fits in the annular groove.

After the foremost ligation ring is moved out of the annular groove, the air discharge port is opened until the ligation ring subsequent to the foremost ligation ring fits in the annular groove. Upon opening of the air discharge port, the air fed from the air introduction means into the cylinder portion via the first air passage is discharged from the air discharge port via the second air passage. As a result, the given amount of air fed from the air introduction means is completely discharged, and the piston member stops moving forward. Meanwhile, the subsequent ligation ring elastically fits in the annular groove and blocks the air discharge port and remains in the groove until the piston member is moved forward again by a given amount of air introduced from the air introduction means. Thus, according to the present invention, only by feeding a given amount of air from the air introduction means, it is ensured that the ligation rings can be released from the front end of the inner cylindrical portion one at a time. When ligation is still carried out on other varicose veins, the above procedure is repeated, and ligation can be continued without taking the endoscope in and out of the body cavity of patient.

Further, in the present invention, at the front end of the inner cylindrical portion, a tapered portion whose diameter gradually decreases from the top of an internal wall on one side of the annular groove to the front edge of the inner cylindrical portion so as to guide the ligation ring which has gone over the top of the internal wall of the annular groove in a direction to release the ring from the front end of the inner cylindrical portion is formed, and the tapered portion guides a ligation ring toward the front edge of the inner cylindrical portion when the ligation ring is pushed out of the annular groove and onto the larger-diameter side of the tapered portion which is located on the top of the internal wall of the annular groove by the press force of a subsequent ligation ring and thereby opens the air discharge port.

Thus, by having the tapered portion formed continuously from the annular groove at the front end of the inner cylindrical portion, the foremost ligation ring is guided to the tapered portion after it is moved out of the annular groove and opens the air discharge port. Thereby, the ligation ring can be released from the front end of the inner cylindrical portion smoothly, and the air discharge port can be opened with certainty.

DETAILED DESCRIPTION OF PREFERRED EMBODIMENTS

Figure 1:
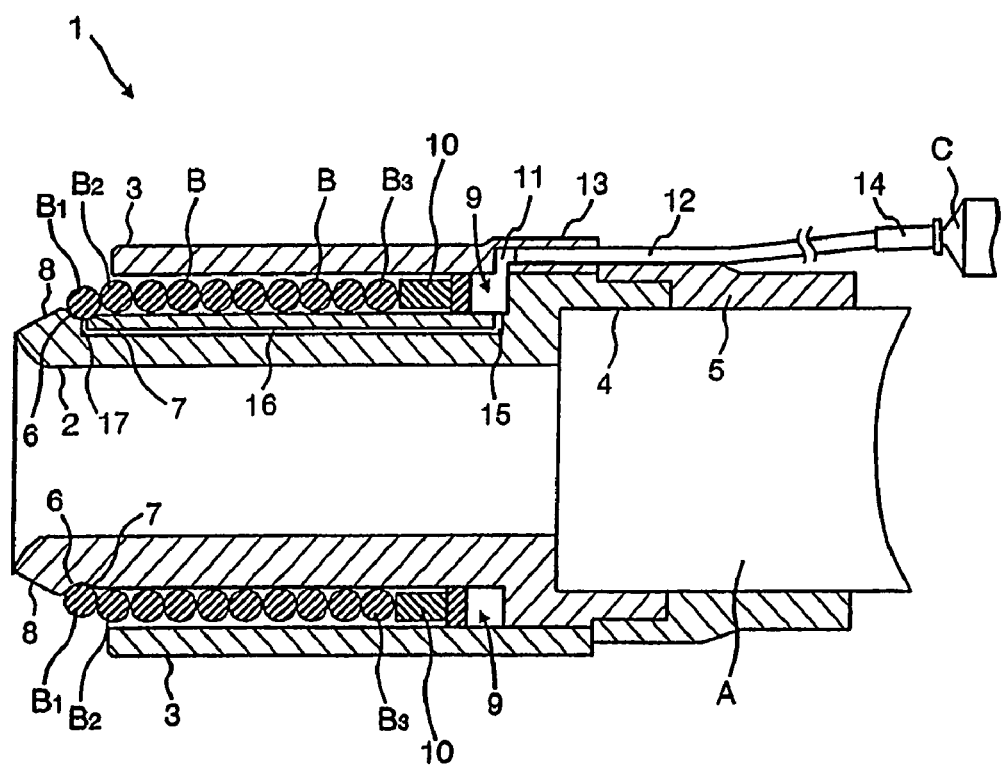
FIG. 1 is an explanatory cross-sectional view showing a ligation treating apparatus of the present embodiment.

A ligation treating apparatus 1 of the present embodiment, as shown in FIG. 1, is connected to the tip of an endoscope A and performs ligation of varicose veins in body cavities such as esophagus and stomach. Firstly, the constitution of the ligation treating apparatus 1 will be described.

The ligation treating apparatus 1 comprises an inner cylindrical portion 2 and an outer cylindrical portion 3 which is provided to the outer side of the inner cylindrical portion 2. At the rear end of the inner cylindrical portion 2, an insertion portion 4 for inserting the tip of the endoscope A is formed, and a cylindrical connection member 5 for firmly connecting the endoscope A inserted into the insertion portion 4 is also provided. On the peripheral wall of the inner cylindrical portion 2, a plurality of ligation rings B are equipped. These ligation rings B are diameter-expanded elastically and aligned and held along the longitudinal direction of the inner cylindrical portion 2 with restoring forces to contract the diameters. Further, on the outer circumference of the front end of the inner cylindrical portion 2, an annular groove 6 is formed. The annular groove 6 is formed to such a depth that the foremost ligation ring B1 can be fitted and released freely. Further, on the rear edge of the annular groove 6, a guide slope 7 for guiding a ligation ring B2 which is subsequent to the foremost ligation ring B1 into the annular groove 6 is formed. On the circumference of the front end of the inner cylindrical portion 2, a tapered portion 8 having a gradually decreasing diameter is formed. When the ligation ring B1 comes off the annular groove 6, the ligation ring B1 moves along the tapered portion 8 due to elastic self-contraction and is released from the inner cylindrical portion 2.

The outer cylindrical portion 3 surrounds the inner cylindrical portion 2 with a given space therebetween (which is set to such a size that the ligation rings B can be moved freely), and a cylinder portion 9 is formed between the inner cylindrical portion 2 and the outer cylindrical portion 3. Inside the cylinder portion 9 is provided an annular piston member 10, and the piston member 10 is in direct contact with the rearmost ligation ring B3. That is, the ligation rings B are accommodated in the cylinder portion 9 together with the piston member 10.

At the rear end of the cylinder portion 9, an air inlet 11 for feeding air for driving the piston member 10 is provided. The air inlet 11 is formed on the internal wall of the outer cylindrical portion 3.

The outer cylindrical portion 3 has a tube connection portion 13 to which the front end of a tube 12 which extends along the endoscope A is connected, and the tube connection portion 13 is communicated with the air inlet 11. At the base end of the tube 12 is provided a connector 14, and a syringe C as air introduction means is connected to the connector 14. A given amount of air forced into the tube 12 by operation of the syringe C is introduced into the cylinder portion 9 via the air inlet 11, and the pressure of the air pushes the piston member 10 forward. The tube 12 and the air inlet 11 constitute a first air passage in the present invention.

Further, at the rear end of the cylinder portion 9, an air outlet 15 for leading air from the cylinder portion 9 is provided. The air outlet 15 is formed on the internal wall of the inner cylindrical portion 2. In addition, a leading slit 16 which is communicated with the air outlet 15 and extends along the longitudinal direction of the inner cylindrical portion 2 is formed. The front end of the leading slit 16 is communicated with an air discharge port 17 which is opened at the bottom of the annular groove 6. The air outlet 15 and the leading slit 16 constitute a second air passage in the present invention.

Figure 2A:
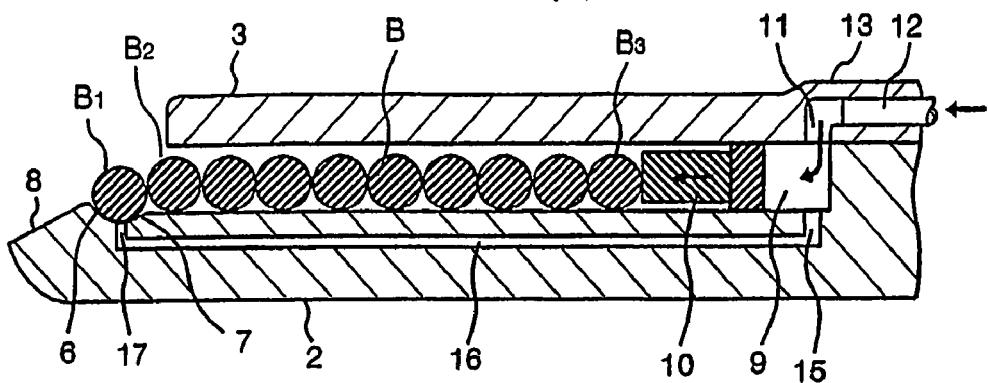
FIG. 2 is an explanatory view showing the operation of the ligation treating apparatus of the present embodiment.

Next, the operation of the ligation treating apparatus 1 according to the present embodiment will be described. The endoscope A is introduced into the body cavity of patient and, firstly, as shown in FIG. 2(a), a varicose vein which is not shown is sucked into the inner cylindrical portion 2 with the foremost ligation ring B1 fitted in the annular groove 6. Since the ligation ring B1 is fitted in the annular groove 6, the air discharge port 17 is closed.

Figure 2B:
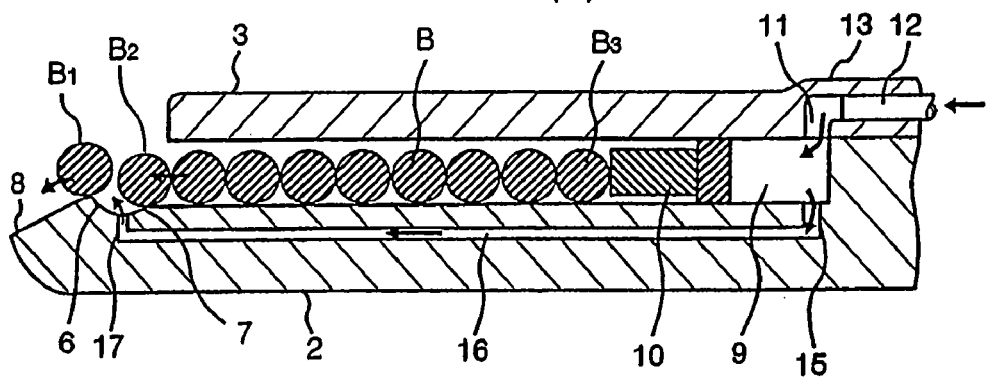

Then, as shown in FIG. 1, a given amount of air is forced into the cylinder portion 9 by means of the syringe C. This causes the piston member 10 to move forward, and the ligation rings B are pushed forward by the pressure of the air. As a result, as shown in FIG. 2(b), the ligation ring B2 which is subsequent to the foremost ligation ring B1 pushes the foremost ligation ring B1 out of the annular groove 6. When the ligation ring B1 moves out of the annular groove 6, the air discharge port 17 which is formed at the bottom of the annular groove 6 is opened. Upon opening of the air discharge port 17, the air in the cylinder portion 9 is discharged from the air discharge port 17 via the air outlet 15 and the leading slit 16. Eventually, all the air goes out of the syringe C, whereby the air pressure drops sharply and the forward movement of the piston member 10 is stopped.

Figure 2C:
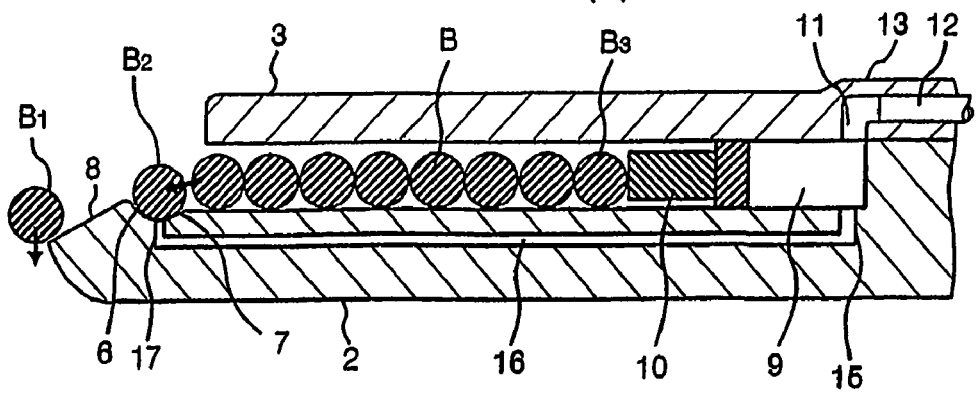

Meanwhile, as shown in FIG. 2(c), the foremost ligation ring B1 which has moved out of the annular groove 6 is released from the front end of the inner cylindrical portion 2 via the tapered portion 8 while elastically contracting so as to ligate the varicose vein which is not shown. Meanwhile, the subsequent ligation ring B2 which is no longer blocked by the ligation ring B1 which has moved out of the annular groove 6 is guided to the annular groove 6 by the guide slope 7 without the press force of the piston member 10 and fits in the annular groove 6 by elastically contracting. Thus, even in the case of abrupt operation of the syringe C, only the foremost ligation ring B1 can be released with certainty from the inner cylindrical portion 2 by a single operation of the syringe C without any problem.

Then, when ligation is to be performed on other varicose veins as well, another varicose vein is sucked into the inner cylindrical portion 2 and the step of introducing a given amount of air by means of the syringe C is carried out with the endoscope A kept in the body cavity of the patient.

Figure 3:
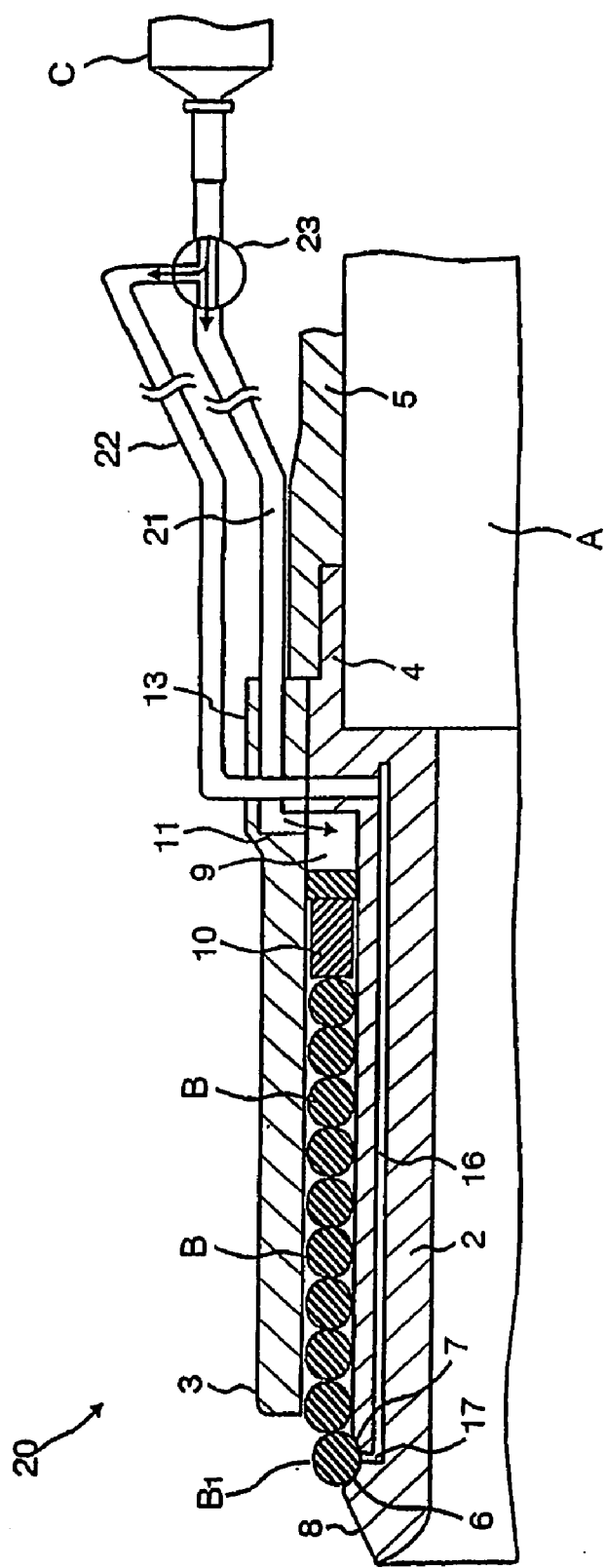
FIG. 3 is an explanatory cross-sectional view showing the substantial parts of a ligation treating apparatus of another embodiment.
Figure 4:
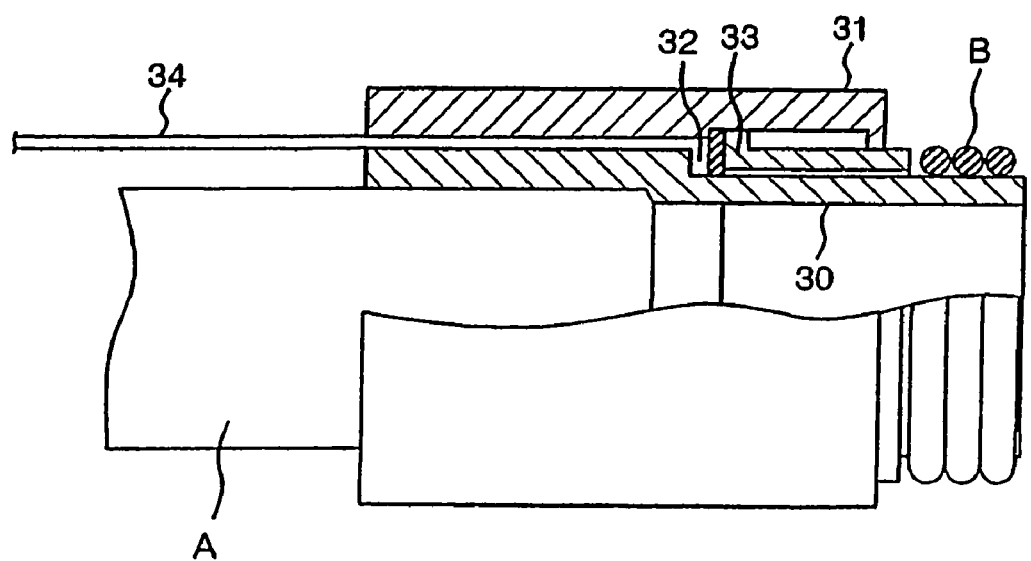
FIG. 4 is an explanatory view of a conventional ligation treating apparatus.

In the present embodiment, the first air passage in the present invention is constituted by the tube 12 and the air inlet 11, and the second air passage in the present invention is constituted by the air outlet 15 and the leading slit 16. Alternatively, the second air passage may adopt the constitution shown in FIG. 3. The same constituents as those described in the above embodiment are given the same reference numbers in FIG. 3, and descriptions thereof will be omitted. That is, a ligation treating apparatus 20, as shown in FIG. 3, has a second tube 22 which branches off from a first tube 21 connected to a tube connection portion 13 communicated with an air inlet 11. The tip of the second tube 22 is inserted in an inner cylindrical portion 2 and connected to a leading slit 16. Further, a switching valve 23 is provided at the point where the second tube 22 branches off. As the switching valve 23, a so-called three-way tap or the like is used. The switching valve 23 connects the first tube 21 to the second tube 22 and can stop flow of air into the second tube 22 by a switching operation.

According to such a constitution, when the foremost ligation ring B1 is not fitted in an annular groove 6, such as at the start of use of the ligation treating apparatus 20, the switching valve 23 is operated so as to flow air only from the first tube 21. Thereby, air is introduced into the cylinder portion 9, whereby a piston member 10 can be pushed forward so as to fit the foremost ligation ring B1 into the annular groove 6. Meanwhile, at the time of ligation, the switching valve 23 is operated so as to connect the first tube 21 to the second tube 22 (as shown in FIG. 3), whereby the same effect as that of the above ligation treating apparatus 1 can be obtained.

INDUSTRIAL APPLICABILITY

The present invention has a plurality of ligation rings and is capable of performing ligation on varicose veins on multiple sites quickly and releasing the ligation rings from the front end of an inner cylindrical portion one at a time with certainty. Therefore, it can be used as a ligation treating apparatus to be attached to the tip of an endoscope.

The invention claimed is:

1. A ligation treating apparatus which is attached to a tip of an endoscope for carrying out ligation of a varicose vein, comprising:

an inner cylindrical portion which is connected to the tip of the endoscope;

a plurality of ligation rings which are aligned and held on an outer circumference of the inner cylindrical portion with diameters thereof elastically expanded and are guided by the inner cylindrical portion and movable toward the front end of the inner cylindrical portion;

an outer cylindrical portion which surrounds the inner cylindrical portion via the ligation rings and forms a cylinder portion by use of space between the inner cylindrical portion and the outer cylindrical portion;

an annular piston member which is provided in the cylinder portion in direct contact with a rearmost ligation ring and can push the ligation rings toward the front end of the inner cylindrical portion;

a first air passage for introducing air to drive the piston member forward into the cylinder portion on the rear side of the piston member;

air introduction means for forcing a given amount of air into the cylinder portion via the first air passage;

an annular groove which is formed along the entire outer circumference of a front end of the inner cylindrical portion so that the foremost ligation ring is fitted and held in the groove releasably;

a second air passage which branches off from the first air passage and extends along the inner cylindrical portion; and an air discharge port which is communicated with the second air passage and opened at the bottom of the annular groove;

wherein the air discharge port is blocked by a ligation ring fitted in the annular groove and opened when the ligation ring is moved out of the annular groove by the press force of the piston member and discharges air fed from the air introduction means to the cylinder portion so as to stop the piston member.

2. The apparatus according to claim 1, wherein at a front end of the inner cylindrical portion, a tapered portion whose diameter gradually decreases from the top of an internal wall on one side of the annular groove to the front edge of the inner cylindrical portion so as to guide the ligation ring which has gone over the top of the internal wall of the annular groove in a direction to release the ring from the front end of the inner cylindrical portion is formed, and the tapered portion guides a ligation ring toward the front edge of the inner cylindrical portion when the ligation ring is pushed out of the annular groove and onto the larger-diameter side of the tapered portion which is located on the top of the internal wall of the annular groove by the press force of a subsequent ligation ring and thereby opens the air discharge port.

3. A ligation treating apparatus, comprising:

an inner cylindrical portion configured to be connected to a tip of an endoscope;

an outer cylindrical portion surrounding the inner cylindrical portion with a predetermined space therebetween such that litigation rings can be moved along the predetermined space towards a tapered end portion of the inner cylindrical portion;

a piston member disposed within the space between the inner and outer cylindrical portions and configured to push litigation rings installed within the space to the tapered end portion of the inner cylindrical portion;

a first air passage configured to introduce a medium to drive the piston member forward to thereby push litigation rings installed within the space to the tapered end portion of the inner cylindrical portion; and a second air passage which branches off from the first air passage, extends along the inner cylindrical portion below the space between the inner and outer cylindrical portions, and opens at an air discharge position where a litigation ring closest to the tapered end of the inner cylindrical portion rests in a groove formed in the inner cylindrical portion before being ejected onto the tapered end;

wherein when the medium is introduced into the first air passage, the medium drives the piston member forward to push the litigation ring resting in the groove of the inner cylindrical portion onto the tapered end of the inner cylindrical portion and thus opening the air discharge position of the second air passage such that a pressure of the medium pressing the piston member is reduced and a next litigation ring is pushed into the groove of the inner cylindrical portion.

4. The apparatus according to claim 3, wherein the medium is air.

5. The apparatus according to claim 3, wherein a plurality of ligation rings are aligned and held on an outer circumference of the inner cylindrical portion with diameters thereof elastically expanded and are guided by the inner cylindrical portion and movable toward the tapered end of the inner cylindrical portion.

6. The apparatus according to claim 3, wherein the second air passage branches off from the first air passage at a beginning of the space between the inner and outer cylindrical portions farthest from the tapered end.

7. The apparatus according to claim 3, wherein the second air passage branches off from the first air passage at a position outside of the inner and outer cylindrical portions such the first and second air passages are completely independent of each other until the second air passage meets the first air passage at the discharge opening of the second air passage.

8. The apparatus according to claim 3, further comprising:
a switching valve configured to switch between providing the medium to the first or second air passages.

9. The apparatus according to claim 8, wherein at a start of the ligation apparatus, the switching valve is switched to provide the medium only to the first air passage such that a first ligation is pushed onto the groove formed in the inner cylindrical portion, and then the switching valve is switched to provide the medium to only the second air passage such that the first ligation is pushed out of the groove and onto the tapered surface.

* * * * *